United States Patent [19]

Ivanov

[11] 4,448,193
[45] May 15, 1984

[54] SURGICAL CLIP APPLIER WITH CIRCULAR CLIP MAGAZINE

[75] Inventor: Konstantin Ivanov, Edison, N.J.

[73] Assignee: Ethicon, Inc., Somerville, N.J.

[21] Appl. No.: 352,836

[22] Filed: Feb. 26, 1982

[51] Int. Cl.³ .......................... F16B 2/10; A61B 17/12
[52] U.S. Cl. ..................................... 128/326; 128/346; 227/DIG. 1
[58] Field of Search .................. 128/325, 326, 334 R, 128/335, 335.5, 346; 227/DIG. 1, DIG. 1 A, DIG. 1 B, DIG. 1 C, 19, 117, 125; 29/243.56; 72/410

[56] References Cited

U.S. PATENT DOCUMENTS

| | | | |
|---|---|---|---|
| 3,075,199 | 1/1963 | Rose et al. | 72/410 |
| 3,307,389 | 3/1967 | Rose et al. | 72/410 |
| 3,601,302 | 8/1971 | Potekhina et al. | 227/DIG. 1 |
| 3,753,438 | 8/1973 | Wood et al. | 128/346 X |
| 4,166,466 | 9/1979 | Jarvik | 227/19 X |
| 4,201,314 | 5/1980 | Samuels et al. | 227/DIG. 1 |
| 4,226,242 | 10/1980 | Jarvik | 128/325 |
| 4,256,251 | 3/1981 | Moshofsky | 128/334 R X |
| 4,316,468 | 2/1982 | Klieman et al. | 128/335 X |
| 4,361,229 | 11/1982 | Mericle | 128/325 X |
| 4,372,316 | 2/1983 | Blake et al. | 128/325 |

FOREIGN PATENT DOCUMENTS 2054026  2/1981  United Kingdom ............... 128/326

Primary Examiner—C. Fred Rosenbaum
Assistant Examiner—Michelle N. Lester
Attorney, Agent, or Firm—Robert L. Minier

[57] ABSTRACT

A method and a repeating instrument are provided for applying a plurality of ligating clips seriatim. Handles are provided for closing a pair of jaws which are normally biased to an open position. A circular magazine is mounted for rotation on the instrument behind the jaws and holds a plurality of clips in a spaced-apart circular array. A flexible pusher member is provided for pushing a clip out of the magazine and into the jaws when the handles are closed. The flexible pusher member is wound on a wheel which is driven by a gear engaged with a gear segment on one of the handles of the instrument. Partial closure of the handles initially withdraws a flexible pusher member from the jaws. Subsequent further closure of the handles acts through a ratchet and pawl mechanism to rotate the magazine to present a new clip in position behind the jaws and in front of the retracted flexible pusher member. At the same time, the jaws of the instrument are squeezed to latch the clip closed about tissue. Subsequent opening of the handles causes the flexible pusher member to be advanced from the magazine to position the new open clip at the jaws.

18 Claims, 10 Drawing Figures

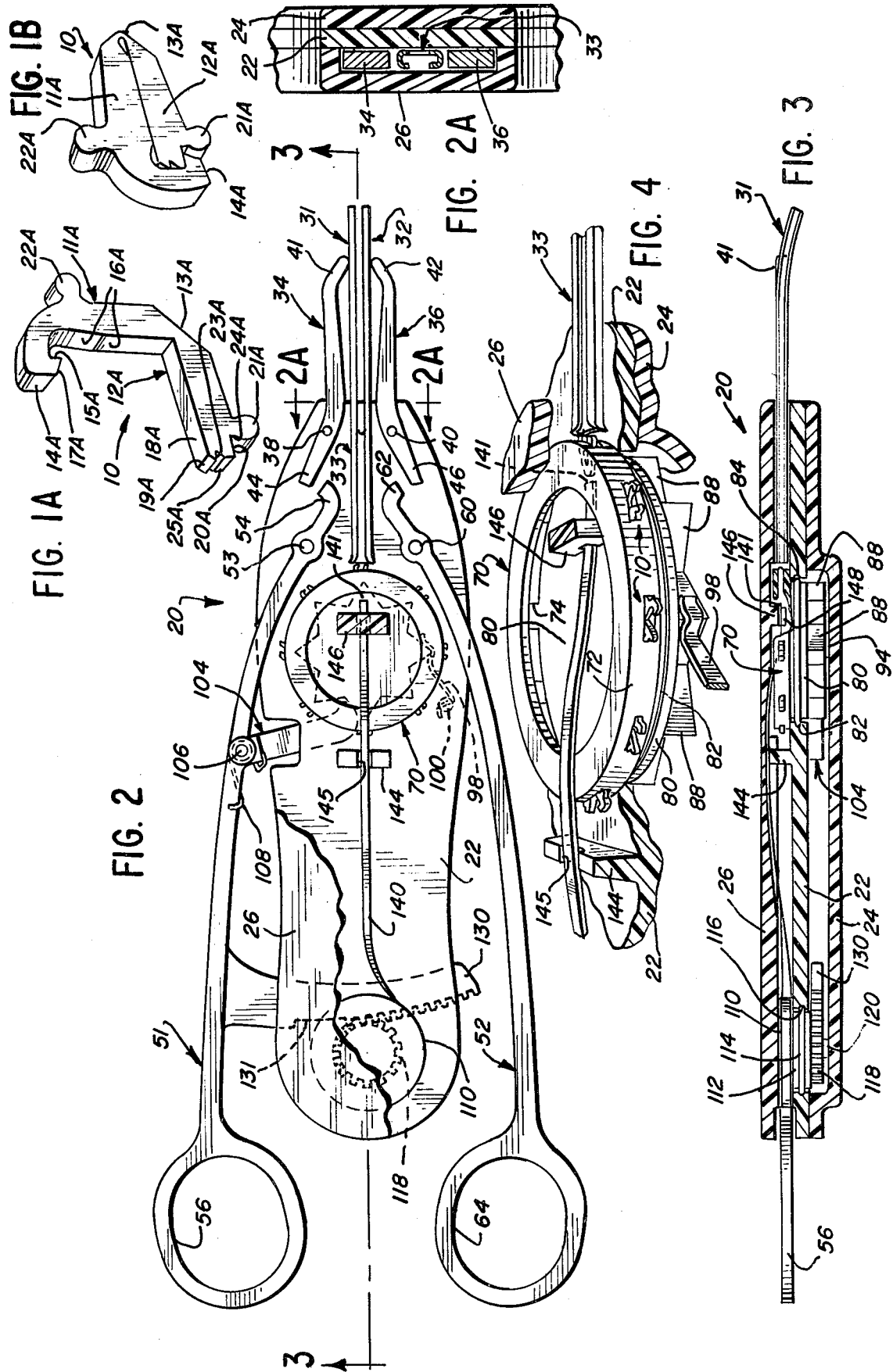

SURGICAL CLIP APPLIER WITH CIRCULAR CLIP MAGAZINE

DESCRIPTION

TECHNICAL FIELD

This invention relates to a surgical instrument for repeatedly applying surgical clamps or clips to tissue, blood vessels, and the like.

BACKGROUND OF THE INVENTION

Clips have been devised for clamping or strangulating various organs, vessels, and other tissue. Clips have been developed for use specifically in strangulating blood vessels in the human body. Such clips are known as hemostatic or ligating clips. The clips may be fabricated from absorbable or nonabsorbable polymeric materials as well as from metal.

A ligating clip is typically C-shaped, U-shaped, or V-shaped with two spaced-apart or diverging legs connected together at one end in a manner that permits the clip to be squeezed together so that the legs of the clip may be clamped around the tissue or blood vessel so as to tightly constrict the tissue or blood vessel. This prevents a substantial amount of fluid from passing through the tissue or blood vessel from one side of the closed clip to the other side of the closed clip.

Typically, the clip is made of a material and/or has a configuration that enables the clip, once it has been forced closed, to remain set or latched and maintain the closed orientation without outside intervention. For example, if the clip is made from a metal material, the clip can be deformed to the closed position. If the clip is made from a thermoplastic material, the legs may be connected by a resilient hinge portion and the distal ends of the legs may be provided with latch means for holding the legs together in a closed position when the legs of the clip are squeezed together around the tissue or blood vessel.

A variety of instruments for applying such surgical clips have been developed or proposed in the past. A number of such instruments are discussed and disclosed in the copending patent application Ser. No. 208,368, filed on Nov. 19, 1980. Such instruments typically include a magazine or cartridge which may or may not be disposable and which holds a plurality of clips. The clips are supplied from the cartridge to jaws of the instrument one at a time for application to the tissue or blood vessel.

U.S. Pat. No. 3,753,438 discloses an applicator for applying clips to suturing thread during the suturing of skin wounds. The clips are carried in a cartridge in the instrument. A clip is foced forwardly from the cartridge to a position between the instrument jaws by a slide which is operated by a handle. After the clip is positioned within the jaws, the handles of the instrument are squeezed together to squeeze the clip legs together.

It would be desirable to provide an improved method for applying clips. It would be desirable to provide such an instrument with the capability for accommodating a plurality of clips and for automatically feeding the clips seriatim into jaws where the clips may be compressed about tissue, such as blood vessels and the like. It would be beneficial if the clips were contained within a magazine or cartridge and it would be advantageous if the magazine could be easily inserted into, and removed from, the instrument. It would also be beneficial if the instrument could accommodate a magazine of relatively simple design having relatively low material costs and low fabrication costs so that the magazine may be disposable.

It would also be desirable to provide an instrument for applying clips wherein the clips could be arranged in a relatively compact orientation in order to provide an efficient and economical magazine structure. It would be beneficial if the instrument could be provided with means for moving the clips forwardly individually from the magazine to the jaws and in a manner that would avoid imposition of an undesired force on the tissue during application of each clip. Further, elimination of a feeding force on the clip during application of the clip would reduce the possibility that the clip might twist or turn during the application of the clip to the tissue.

It would also be desirable to provide an instrument for applying ligating clips in which the instrument could be actuated by means of scissors-type handles in the same manner as a number of other widely used surgical instruments and in the manner to which surgeons have become accustomed over the years.

SUMMARY OF THE INVENTION

A method is provided for applying ligating clips with an instrument. The clips are maintained in a circular array in a magazine which is rotated as necessary to align a new clip with certain instrument mechanisms.

A preferred embodiment of the present invention is incorporated in a medical instrument for applying the clips, including ligating clips made from a thermoplastic material. The clips each typically have two legs connected together at one end of the clip and adapted to be opened or spread apart at the other end.

The instrument includes a frame, first and second jaws mounted to the frame in confronting relationship for movement away from each other into an open position to receive one of the clips and toward each other into a closed position for closing the clip. Jaw biasing means is provided for biasing the jaws outwardly away from each other and into the open position.

A jaw actuating means is provided for being operated to permit the movement of the jaws away from each other into the open position under the influence of the jaw biasing means and for being operated through a lost motion phase to effect movement of the jaws toward each other from the open position into the closed position following the termination of the lost motion phase.

A magazine is provided with means for mounting the magazine on the frame for rotation relative to the frame. The magazine defines a plurality of clip storage regions arranged in a generally circular array. Each clip storage region defines an inner access opening at an inner radius of the circular array and an outer access opening at an outer radius of the circular array. Each clip storage region is adapted to hold one of the clips with the clip leg connection end adjacent the inner access opening and with the clip leg distal ends adjacent the outer access opening.

Means is provided on the frame for releasably retaining the magazine against inadvertent rotational movement after the magazine has been rotated to align any one of the magazine clip storage regions with the first and second jaws.

A magazine rotating means is provided, responsive to the operation of the jaw actuating means to close the jaws, for incrementally rotating the magazine to move one of the clip storage regions out of registration with the jaws and to move the next adjacent clip storage region into registration with the jaws.

The instrument also includes a clip pushing means, responsive to the operation of the jaw actuating means, for (1) advancing into one of the magazine clip storage regions in registration with the jaws and moving the clip out of the clip storage region and into position between the jaws when the jaw actuating means is operated to permit the opening of the jaws, and (2) withdrawing from the jaws behind the inner access opening of one of the clip storage regions in registration with the jaws when the jaw actuating means is operated through the lost motion phase prior to the closure of the jaws.

Numerous other advantages and features of the present invention will become readily apparent from the following detailed description of the invention and of one embodiment thereof, from the claims, and from the accompanying drawings.

BRIEF DESCRIPTION OF THE DRAWINGS

In the accompanying drawings forming part of the specification, and in which like numerals are employed to designate like parts throughout the same, FIG. 1A is a perspective view of one type of clip (shown open) that may be applied to tissue with the instrument of the present invention;

FIG. 1B is a perspective view of the clip of FIG. 1A shown in a latched closed position;

FIG. 2 is a top plan view of the instrument of the present invention with portions of the frame top cover plate broken away to better illustrate interior details;

FIG. 2A is a greatly enlarged, fragmentary, cross-sectional view taken generally along the plane 2A—2A in FIG. 2;

FIG. 3 is a cross-sectional view taken generally along the plane 3—3 in FIG. 2;

FIG. 4 is a greatly enlarged, perspective, fragmentary view of the central portion of the instrument of the present invention to better illustrate the clip storage magazine in detail;

DESCRIPTION OF THE PREFERRED EMBODIMENT

Figure 5:
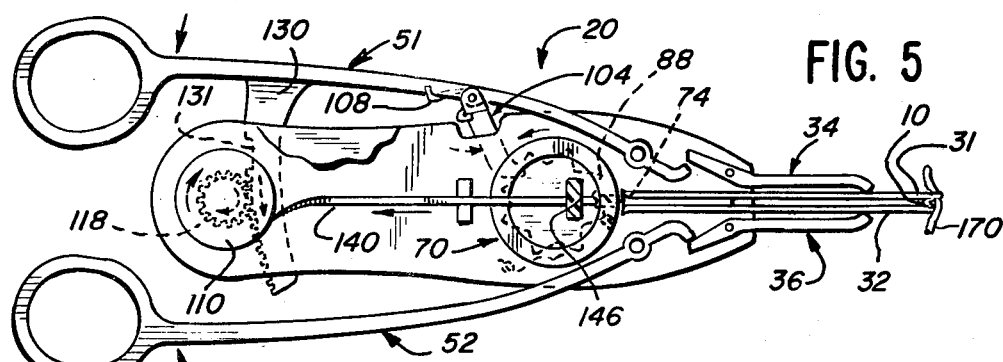
FIGS. 5-7 are plan views of the instrument similar to the plan view of FIG. 2 with portions of the frame top cover plate broken away to better illustrate interior detail and showing various operating positions of the instrument.

This invention may be used in many different forms. The specification and the accompanying drawings disclose a specific embodiment as an example of the use of the invention. The invention is not intended to be limited to the embodiment illustrated, and the slope of the invention will be pointed out in the appended claims.

The precise shapes and sizes of the components herein described are not essential to the invention unless otherwise indicated. The particular shapes and sizes are shown to best illustrate the principles of the invention.

A variety of materials may be used for constructing the illustrated instrument as those skilled in the art will appreciate.

The instrument of the present invention is adapted to apply a variety of ligating clips. One such clip is illustrated in FIGS. 1A and 1B and is designated generally therein by the reference numeral 10. In FIG. 1A, the clip 10 is shown in an open position and in FIG. 1B the clip is shown in a latched closed position.

With continued reference to FIGS. 1A and 1B, the clip 10 is seen to be formed with two leg segments or legs, first leg 11A and second leg 12A, which are joined at the leg connection end of the clip. Preferably, the legs are connected at their proximal ends by a hinge or hinge section 13A. The leg segment 11A terminates at the distal end thereof in a hook member 14A having an inner face 15A substantially parallel to an inner face 16A of the leg 11A and forming an acute angle with an end face 17A.

The leg 12A terminates at the distal end in an end face 19A which forms an obtuse angle with an inner face 18A of the leg 12A. The end face 19A is offset at 23A to form a notch approximately midway between the inner face 18A and a bottom face 20A. Additionally, the leg 12A is squared off at a face 25A to form a substantially right angle with the bottom face 20A.

The length and width of the inner faces 16A and 18A are substantially equal and the face 15A of the hook member 14A is spaced from the inner face 16A of the leg 11A by a distance corresponding to the thickness of the leg 12A between the planes of the inner face 18A and the bottom face 20A.

The clip 10 can be closed or set by pivoting the legs 11A and 12A about the hinge section 13A to bring the inner faces 18A and 16A into opposition. The hook member 14A is deflected by the end face 19A of the leg 12A until the distal end of the leg 12A snaps under the hook member 14A and is thereby locked in place as best illustrated in FIG. 1B. The end face 17A of the hook member 14A and the end face 19A of the leg 12A are angled as illustrated in FIG. 1A to facilitate the passage of the leg 12A past the hook member 14A during clip closure.

The surfaces of the inner faces 16A and 18A may be smooth as illustrated in FIG. 1A, or may be provided with ridges or grooves to increase vessel holding power. The leg 11A may also be undercut at the juncture of the hook member 14A and the inner face 16A as illustrated in FIG. 1A to increase the deflectability of the hook member 14A and increase the space between the hook member 14A and the leg 11A. This compensates for any inward deflection of the hook member 14A during closure which might reduce the clearance between the surfaces 15A and 16A and otherwise interfere with the latching of the clip.

With continued reference to FIGS. 1A and 1B, the leg 12A of the clip 10 includes an outside cylindrical boss 21A extending across the width of the leg 12A near the distal end thereof. Similarly, the leg 11A has a boss 22A extending across the width of the leg 11A near the distal end thereof. The cylindrical bosses 21A and 22A are equidistant from the hinge section 13A so that when the clip 10 is closed, the bosses 21A and 22A define a line perpendicular to the major axis along the length of the clip as best illustrated in FIG. 1B. The boss 21A is spaced from the face 25A a distance sufficient to permit the full engagement of the hook member 14A by the leg 12A when the clip 10 is in the latched closed position (FIG. 1B).

The distal end of the leg 12A forward of the boss 21A is of reduced thickness relative to the thickness immediately to the rear of boss 21A, thereby forming a step 24A between the boss 21A and the bottom surface 20A.

Although the clip 10 has been illustrated as including bosses 21A and 22A on the legs 12 and 11, respectively, it is to be realized that the boss structure may have a different configuration or may be eliminated altogether.

The above-described novel clip structure, when fabricated from a suitable thermoplastic material, is biased to the open position by the resilient hinge portion. Thus, if force is applied to the distal ends of the legs of the open clip so as to move the legs toward one another (but not far enough to latch the clip), then upon removal of the force from the clip legs, the clip legs will return to the substantially fully open orientation.

It is believed that this phenomenon can be used to advantage in certain types of clip applier instruments for guiding and holding the clip in the instrument. Specifically, the legs of the clip may be deflected inwardly toward one another a small amount in a magazine, guide channel, or jaw structure of a clip applier instrument. Owing to the resilience of the hinge joining the two legs, the two legs will exert a force outwardly against the magazine, channel, or jaw structure to thereby provide a small friction holding force which may serve to help maintain the clip in the proper orientation or position within the instrument.

The above-described action of the resilient hinge plastic clip is in contrast with conventional ligating clips fabricated from relatively small diameter wire-like stock. Such metal clips can tolerate substantially no inward deflection of the legs without undergoing permanent deformation. Consequently, such metal clips exhibit no useful degree of resiliency and thus do not have the same inherent capability for providing the frictional holding force that is found in the above-described type of plastic clip.

The precise structure illustrated for the clip 10 is not critical with respect to the operation of the instrument of the present invention that is described hereinafter in detail as being suitable for applying such clips. It is believed that the instrument of the present invention will function well in applying a variety of clips that each have first and second legs joined at their proximal ends.

The novel instrument of the present invention will next be described with reference to FIGS. 2–8 and with reference to applying a clip 10 described above. FIG. 2 illustrates a preferred embodiment of the instrument of the present invention wherein the instrument is designated generally by the reference numeral 20. The instrument 20 has a frame comprising a central frame or plate 22, a bottom frame cover plate 24 (FIG. 3), and a top frame cover plate 26 (FIGS. 2 and 3). The central frame or plate 22 is secured to the bottom frame cover plate 24 and to top frame cover plate 26 by suitable means (not illustrated), such as by snap-fit interlocks, screws, or the like.

Figure 6:
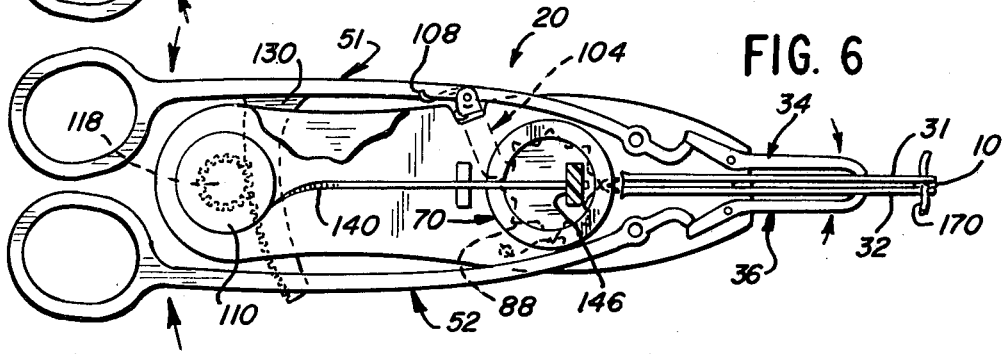

At the forward end of the central frame 22 is mounted a pair of jaws, a first jaw 31 and a second jaw 32. The first and second jaws 31 and 32, respectively, are mounted to the central frame 22 by suitable means (e.g., screws, welds, or the like, not illustrated) in confronting relationship for movement away from each other into a spaced-apart, parallel, open position as illustrated in FIG. 2 to receive one of the clips 10 and toward each other into a closed position as illustrated in FIG. 6 for closing and latching the clip 10.

Preferably, the jaws 31 and 32 are fabricated from a unitary structure of resilient material defining a rear portion 33 that has a substantially C-shaped cross section as best illustrated in FIG. 2A. The rear portion 33 thus defines a channel for receiving one of the clips 10.

Further, the unitary jaw structure includes a forward portion in the form of two spaced-apart, U-shaped channel members defining the jaws 31 and 32. The U-shaped channel members forming each jaw 31 and 32 have sufficient flexibility forward of the rear portion 33 to permit them to be forced to the closed position (by jaw actuating means described in detail hereinafter). The channel members forming each jaw 31 and 32 are sufficiently resilient so that the jaws 31 and 32 move back to the open position when the jaw closing actuating means is operated to permit such opening.

The jaw closing actuating means includes a pair of actuating members 34 and 36. Actuating member 34 is pivotally mounted to central frame 22 about a shaft 38. Similarly, actuating member 36 is pivotally mounted to central frame 22 about a shaft 40. The actuating member 34 has a forward distal end portion 41 adapted to engage the jaw 31 and has a rear portion 44 extending rearwardly and outwardly away from the jaw 31. Similarly, the actuating member 36 has a forward distal end portion 42 adapted to engage the jaw 32 and has a rear portion 46 extending rearwardly and outwardly away from the jaw 32.

The actuating members 34 and 36 are operated by first and second handles 51 and 52, respectively. The first handle 51 is pivotally mounted to the central frame 22 about a pivot shaft 53. The handle 51 includes an engaging portion 54 extending beyond the pivot shaft 53 and is adapted to engage the rearwardly extending portion 44 of the actuating member 34. The handle 51 also includes a thumb or finger ring 56 by which the handle is operated.

Similarly, the second handle 52 is pivotally mounted to the central frame 22 about a pivot shaft 60. The second handle 52 has an engaging portion 62 extending forwardly beyond the pivot shaft 60 for engaging the rearwardly extending portion 46 of the actuating member 36. The second handle 52 also includes a thumb or finger ring 64.

When the first and second handles 51 and 52, respectively, are pivoted to bring the finger rings closer together, the engaging portions 54 and 62 move outwardly to engage the rearwardly extending portions 44 and 46, respectively, of the actuating members 34 and 36, respectively. This causes the actuating members 34 and 36 to pivot so that the forward distal end portions 41 and 42 are forced against the first and second jaws 31 and 32, respectively, to move the jaws toward each other from the open position (illustrated in FIG. 2) to the closed position (illustrated in FIG. 6).

Figure 8:
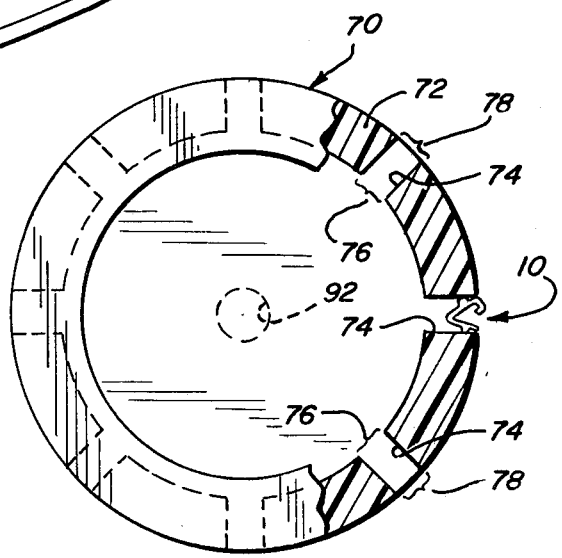
FIG. 8 is a greatly enlarged, partial cross-sectional view of the clip storage magazine used in the instrument of the present invention.

As best illustrated in FIGS. 2–4, the instrument 20 includes a magazine 70. The magazine 70 has a generally circular configuration with a circumferential annular wall 72 as best illustrated in FIG. 8. The annular wall 72 defines a plurality of clip storage regions or cavities 74 which are each adapted to contain or hold one clip 10. The storage regions 74 are arranged in a generally circular array in the wall 72 around the magazine 70. Each clip storage region 74 defines (1) an inner access opening 76 (FIG. 8) at the inner radius of the circular array of storage regions (at the inner radius of the wall 72) and (2) an outer access opening 78 at the outer radius of the array of clip storage regions 74 (at the outer radius of the wall 72). A clip 10 is positioned within each storage region 74 with the clip hinge adjacent the inner access opening 76 and with the ends of the clip legs adjacent the outer access opening 78 as best illustrated in FIGS. 4 and 8.

As best illustrated in FIGS. 3 and 4, the magazine 70 also includes a central cylindrical region 80 which has a circumferentially disposed annular rib 82 received in a complementary channel 84 in the central frame 22. Projecting downwardly below the magazine central portion 80 is a circular array of ratchet teeth 88 which are disposed in a circular array below the circular array of clip storage regions 74.

In the bottom of the magazine 70 at the center of the ratchet teeth 88 is a cylindrical recess or bore 92 (visible in FIG. 8 only) located so that the ratchet teeth 88 are concentric about the bore 92 which defines an axis of rotation for the magazine. The bore 92 is adapted to receive a post 94 projecting upwardly from the bottom frame cover plate 24 (FIG. 3). The magazine 70 is releasably mounted on the post 94 for rotation relative to the bottom frame cover plate 24 and may be removed after all of the clips have been applied by the instrument. To this end, the annular rib 82 may be constructed of resilient material to accommodate insertion of the magazine 70 into, and removal of the magazine 70 from, the channel 84 in the central frame 22. The empty magazine 70, once it is removed, may then be refilled and loaded back into the same or a different instrument.

A spring or spring means 98 (FIGS. 2 and 4) is carried on the bottom frame cover plate 24 for engaging one of the ratchet teeth 88 after the magazine 70 is rotated (by means described hereinafter) to align any one of the magazine clip storage regions 74 with the first and second jaws 31 and 32, respectively. The spring 98 is formed with an angle at its distal end to engage the apex of a ratchet tooth 88 and is secured at its other end to a post 100 (FIG. 2) which projects upwardly from the bottom frame cover plate 24. The spring 98 functions to releasably retain the magazine 70 against inadvertant rotational movement.

As best illustrated in FIG. 2, a pawl 104 is carried on the first handle 51 for engaging the magazine ratchet teeth 88 when the handles are moved toward each other. Specifically, the pawl 104 is pivotally mounted about 106 to the handle 51. Further, a biasing means or spring 108 (FIG. 2) is provided on the handle 51 to bias the pawl 104 against the ratchet teeth 88.

The magazine teeth 88, the pawl 104, and the pawl spring 108 function as means responsive to the operation of the handles 51 and 52 for rotating the magazine 70. The magazine clip storage regions 74 and the ratchet teeth 88 on the magazine 70 are arranged so that the movement of the first and second handles 51 and 52, respectively, toward each other, causes the pawl 104 to engage the ratchet teeth 88 and to incrementally rotate the magazine 70 so as to move one of the clip storage regions 74 out of registration with the jaws 31 and 32 and so as to move the next adjacent clip storage region into registration with the jaws.

A novel mechanism or clip pushing means, responsive to the operation of the handles 51 and 52, is provided for moving the clips 10 from the magazine 70 to the jaws 31 and 32. Specifically, as best illustrated in FIGS. 2 and 3, a wheel 110 is mounted for rotation in the central frame 22. The wheel 110 has an intermediate cylindrical portion 112 (FIG. 3) with an annular flange 114 adapted to be received in a complementary annular channel 116 of the central frame 22. Projecting downwardly below the cylindrical central portion 112 is a circular gear 118. The wheel 110, the intermediate portion 112, and the gear 118 preferably form a unitary assembly that is mounted for rotation about a shaft 120 that projects upwardly from the bottom frame cover plate 24.

As best illustrated in FIGS. 2 and 3, a gear segment 130 is provided on the first handle 51 and is engaged with the circular gear 118 below the wheel 110. Thus, when the handles 51 and 52 are moved together, the wheel 110 is rotated in one direction (clockwise as viewed in FIG. 2) and when the handles are moved apart, the wheel 110 is moved in a second, opposite direction (counterclockwise as viewed in FIG. 2). the gear segment 130 defines a slat region or notch 131 inwardly of the gear segment teeth. The notch 131 has a depth equal to, or greater than, the length of the gear segment teeth. During the last portion of the movement of the handles 51 and 52 toward one another, the teeth of the gear segment 130 disengage from the gear 118 as the notch 131 is carried adjacent the gear 118.

A flexible pusher member 140, in the form of a flexible metal band or spring, is secured to, and partially wound around, the wheel 110. The flexible pusher member 140 has at least a forward end or end portion 141 (FIGS. 2-4) adapted to enter into the magazine clip storage regions 74. As best illustrated in FIG. 2, the flexible pusher member 140 is twisted through an angle of 90 degrees as it unwinds from the wheel 110 and extends forwardly into the magazine 70.

As best illustrated in FIG. 4, the central frame 22 includes a guide wall 144 defining a guide channel 145 rearwardly of the magazine 70 for guiding the flexible pusher member 140 over the top of magazine 70. Further, as best illustrated in FIGS. 3 and 4, the top frame cover plate 26 has a downwardly projecting guide member 146 which defines a guide channel 148 (FIG. 3) for guiding the flexible pusher member 140 adjacent the inner radius of the circular array of clip storage regions 74 and in registration with the jaws 31 and 32.

The sequence of operation of the instrument 20 will next be described with reference to FIGS. 5-7. FIG. 5 illustrates the instrument 20 with a clip 10 already in position at the end of the jaws 31 and 32 and with the still open clip 10 located around a blood vessel 170. In this orientation, the instrument handles 51 and 52 are partially, but not fully, closed. The magazine 70 is oriented with an empty clip storage region 74 aligned with the jaws 31 and 32. The aligned storage region 74 is empty because the clip 10 has already been moved from the magazine 70 to the ends of the jaws 31 and 32. Also, in the orientation illustrated in FIG. 5, the flexible pusher member 140 is retracted from the jaws and is oriented with the distal end located just behind the inner access opening of the aligned empty clip storage region 74.

When it is desired to apply the clip 10 to the blood vessel 170, the handles 51 and 52 are moved closer together. This causes the actuating members 34 and 36 to pivot toward each other to close the jaws 31 and 32 and thus latch the clip 10 closed about the vessel 170 (FIG. 6). As this happens, the pawl 104, being engaged with a ratchet tooth 88, causes the magazine 70 to rotate (in a counterclockwise direction as viewed in FIGS. 5 and 6) to move the next clip storage region (which contains a new open clip) into registration with the jaws 31 and 32.

As the handles 51 and 52 are closed from the position illustrated in FIG. 5 to the clip closing position illustrated in FIG. 6, an additional small amount of the flexible pusher member 140 is wound around the wheel 110. This withdraws the distal end of the flexible pusher 140 rearwardly a small additional amount. However, the distal end of the flexible pusher member 140 is not withdrawn rearwardly of the guide 146 because the circular gear 118 rotates out of engagement with the gear segment 130 and the toothless notch 131 of the gear segment 130 is moved adjacent the gear 118 as the handles 51 and 52 approach the point of full closure.

Figure 7:
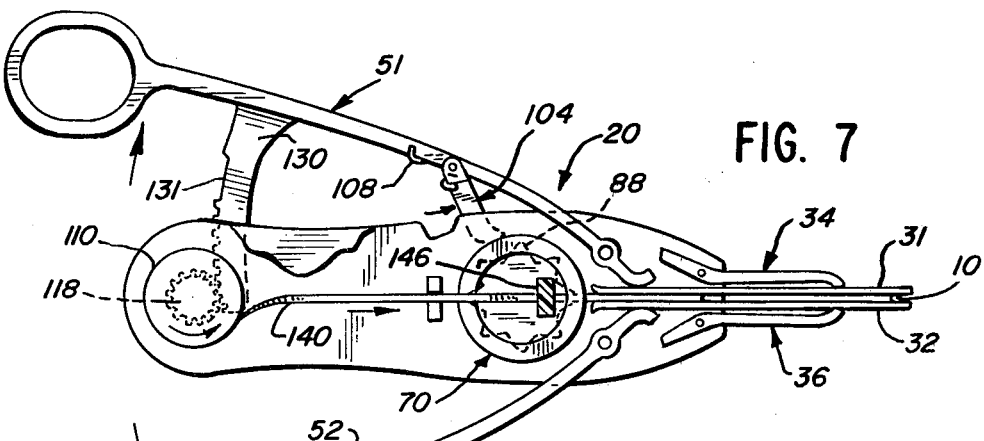

When the handles 51 and 52 are subsequently moved apart to their maximum wide open position as illustrated in FIG. 7, the jaws 31 and 32 spring to the open position and release the closed clip. Further, the gear segment 130 causes the wheel 110 to be rotated (counterclockwise as viewed in FIG. 7) to unwind the flexible pusher 140 and advance the flexible pusher from the fully retracted position illustrated in FIG. 6 to the fully advanced position illustrated in FIG. 7.

As the flexible pusher member 140 advances, the distal end 141 enters into the clip storage region aligned with the jaws and pushes the new clip from the clip storage region. The pusher member 140 continues to advance and push the clip along to the distal end of the jaws 31 and 32 for placement about another blood vessel.

As the handles 51 and 52 are being opened to advance the pusher member 140, the pawl 104 on the handle 51 is pulled past the teeth 88. Finally, the pawl 104 is carried outwardly away from the magazine 70. Once the handles have been moved to the wide open position illustrated in FIG. 7, the pawl 104 is positioned completely out of engagement with any of the ratchet teeth 88. The pawl 104 is then biased (in the counterclockwise direction as viewed in FIG. 7) by the spring 108 so that the leading end of the pawl 14 is in position to engage one of the ratchet teeth 88 when the handles are subsequently moved together to close the clip.

It will be apparent that the pawl 104, being spaced from the ratchet teeth 88 when the instrument handles are wide open (FIG. 7), does not immediately engage the ratchet teeth 88 when the handles are subsequently moved toward one another. The pawl 104 does not engage the ratchet teeth 88 until the handles have moved toward each other through a lost motion phase or range a predetermined amount (to the point illustrated in FIG. 5). This permits the flexible pusher member 140 to be retracted (by the rotating wheel 110) from the jaws and clear of the magazine 70 before the magazine 70 is subsequently caused to be incrementally rotated to align the next clip storage region 74 with the jaws.

If desired, the handles 51 and 52 may be left in the full position illustrated in FIG. 7 until it is desired to latch the new clip 10 closed. Alternatively, the handles may be partially closed to the position illustrated in FIG. 5. This would cause the flexible pusher member 140 to be retracted behind the now-empty clip storage region. Further movement of the handles toward each other will initiate another clip closure sequence as explained above with reference to FIGS. 5 and 6.

The instrument of the present invention may be used to apply other types of clips, including metal hemostatic clips, that are utilized in surgical procedures. For example, such clips may be narrow U-shaped or V-shaped strips formed of tantalum or stainless steel which are capable of being deformed and which possess sufficient strength to retain the deformation when clamped about a duct, such as a blood vessel.

From the foregoing, it will be observed that numerous variations and modifications may be effected without departing from the true spirit and scope of the novel concept of the invention. It is to be understood that no limitations with respect to the specific apparatus illustrated herein is intended or should be inferred. It is, of course, intended to cover by the appended claims all such modifications as fall within the scope of the claims.

What is claimed is:

1. A repeating medical instrument for applying a plurality of ligating clips seriatim about tissue wherein each said clip is initially provided in an open state, each said open clip comprising first and second legs joined at their proximal ends by a resilient hinge and being spaced apart at their distal ends with said legs having latch means at said distal ends for holding said clip closed in clamping engagement about said tissue when said legs are squeezed together, said instrument comprising:

a frame;
first and second jaws mounted to said frame in confronting relationship for movement away from each other into an open position to receive one of said clips and toward each other into a closed position for closing and latching said one clip;
jaw biasing means for biasing said jaws outwardly away from each other and into said open position;
a pair of actuating members pivotally mounted to said frame, each said actuating member having a forward distal end portion adapted to engage one of said jaws and having a rear portion extending outwardly away from said one jaw;
first and second handles mounted to said frame for pivotal movement, each of said first and second handles including an engaging portion extending beyond its pivot axis and adapted to engage said rear portion of one of said actuating members whereby, when said first and second handles are moved toward each other, said engaging portions of each of said first and second handles move outwardly to engage said rear portions of said actuating members to force said forward distal end portions of said actuating members against said first and second jaws to move said jaws toward each other from said open position into said closed position;
a magazine and means for releasably mounting said magazine on said frame for rotation relative to said frame, said magazine defining a plurality of clip storage regions arranged in a generally circular array, each said clip storage region defining an inner access opening at an inner radius of said circular array and an outer access opening at an outer radius of said array, each said clip storage region being adapted to hold one of said clips with said clip hinge adjacent said inner access opening and with said clip leg distal ends adjacent said outer access opening, said magazine further including a circular array of ratchet teeth concentric about the axis of rotation of said magazine;
spring means carried on said frame for engaging one of said ratchet teeth when said magazine is rotated to align any one of said magazine clip storage regions with said first and second jaws;
a pawl carried on one of said handles for engaging said magazine ratchet teeth after said handles have been moved toward each other a predetermined amount;

biasing means associated with said pawl and the handle on which said pawl is carried for biasing said pawl into engagement with said magazine ratchet teeth;

said magazine clip storage regions and ratchet teeth on said magazine being arranged so that the movement said first and second handles toward each other beyond a predetermined point causes said pawl to engage said ratchet teeth and incrementally rotate said magazine to move one of said clip storage regions out of registration with said jaws and to move the next adjacent clip storage region into registration with said jaws;

a wheel mounted for rotation to said frame;

a flexible pusher member secured to and partially wound around said wheel, said flexible pusher member having at least a forward end adapted to enter into one of said magazine clip storage regions in registration with said jaws and to move said clip out of said clip storage region into said jaws;

a circular gear connected with said wheel for rotation therewith; and a gear segment on one of said first and second handles and engaged with said circular gear for (1) rotating said wheel in a first direction when said handles are moved together to withdraw said flexible pusher member from said jaws and behind said inner access opening of one of said clip storage regions in registration with said jaws and (2) rotating said wheel in a second, opposite direction when said handles are moved apart whereby said flexible pusher member is advanced through one of said clip storage regions in registration with said jaws and between said jaws to position one of said clips at said jaws.

2. The instrument in accordance with claim 1 in which said frame includes a guide channel rearwardly of said magazine for guiding said flexible pusher member.

3. The instrument in accordance with claim 1 in which said frame includes a cover plate releasably disposed over said magazine and in which said cover plate includes a downwardly projecting guide member defining a guide channel for guiding said flexible pusher member adjacent the inner radius of said circular array of clip storage regions in registration with said jaws.

4. The instrument in accordance with claim 1 in which said jaws are fabricated from a unitary structure of resilient material, in which a rear portion of said structure has a substantially C-shaped cross section defining a channel for receiving one of said clips, and in which a forward portion of said structure includes two spaced-apart, U-shaped channel members extending forwardly of said rear portions of said structure for defining said jaws and having sufficient flexibility for the jaws to be closed by said actuating members while having sufficient resilience to move said jaws to said open position when said handles are opened a sufficient amount.

5. The instrument in accordance with claim 1 in which said magazine has a generally circular configuration, in which said ratchet teeth are integrally formed on the bottom of said magazine, in which said frame includes an upstanding post, and in which said means for releasably mounting said magazine for rotation on said frame includes a bore for receiving said upstanding post.

6. The instrument in accordance with claim 1 in which said wheel is mounted for rotation about an axis parallel to the axis of rotation of said magazine and in which said flexible pusher member is twisted through an angle of about 90 degrees.

7. A medical instrument for applying a plurality of ligating clips seriatim about tissue wherein each said clip is initially provided in an open state, each said open clip comprising first and second legs joined at their proximal ends by a resilient hinge and being apart at their distal ends with said legs having latch means at said distal ends for holding said clip closed in clamping engagement about said tissue when said legs are squeezed together, said instrument comprising:

a frame;

first and second jaws mounted to said frame in confronting relationship for movement away from each other into an open position to receive one of said clip and toward each other into a closed position for closing and latching said one clip;

jaw biasing means for biasing said jaws outwardly away from each other from said closed position and into said open position;

jaw actuating means for being operated to permit the movement of said jaws away from each other into said open position under the influence of said jaw biasing means and for being operated through a lost motion phase to effect movement of said jaws toward each other from said open position into said closed position following the termination of said lost motion phase;

a magazine and means for mounting said magazine on said frame for rotation relative to said frame, said magazine defining a plurality of clip storage regions arranged in a generally circular array, each said clip storage region defining an inner access opening at an inner radius of said circular array and an outer access opening at an outer radius of said array, each said clip storage region being adapted to hold one of said clips with said clip hinge adjacent said inner access opening and with said clip leg distal ends adjacent said outer access opening, said magazine further including a circular array of ratchet teeth concentric about the axis of rotation of said magazine;

means carried on said frame for releasably retaining said magazine against inadvertent rotational movement after said magazine has been rotated to align any one of said magazine clip storage regions with said first and second jaws;

a pawl carried on said jaw actuating means for engaging said magazine ratchet teeth when said jaw actuating means is operated to close said jaws;

biasing means associated with said pawl and with said jaw actuating means for biasing said pawl into engagement with said magazine ratchet teeth;

said magazine clip storage regions and ratchet teeth on said magazine being arranged so that operation of the said jaw actuating means to close said jaws causes said pawl to engage said ratchet teeth and incrementally rotate said magazine to move one of said clip storage regions out or registration with said jaws and to move the next adjacent clip storage region into registration with said jaws; and clip pushing means responsive to said jaw actuating means for (1) advancing into one of said magazine clip storage regions in registration with said jaws and moving said clip out of said clip storage region and into position between said jaws when said jaw actuating means is operated to permit the opening of said jaws, and for (2) withdrawing from said jaws and behind said inner access opening of one of said clip storage regions in registration with said jaws as said jaw actuating means is operated through said lost motion phase prior to the closure of said jaws.

8. The instrument in accordance with claim 7 in which said clip pushing means includes a wheel mounted for rotation on said frame, a flexible member partially wound on said wheel, and means for rotating said wheel in either of two directions.

9. The instrument in accordance with claim 7 in which said jaws are fabricated from a unitary structure of resilient material, in which a rear portion of said structure has a substantially C-shaped cross section defining a channel for receiving one of said clips, and in which a forward portion of said structure includes two spaced-apart, U-shaped channel members extending forwardly of said rear portion of said structure for defining said jaws and having sufficient flexibility for the jaws to be closed by said jaw actuating means while having sufficient resilience to move said jaws to said open position when said jaw actuating means is operated to permit movement of said jaws away from each other.

10. The instrument in accordance with claim 7 in which said magazine has a generally circular configuration, in which said ratchet teeth are integrally formed on the bottom of said magazine, in which said frame includes an upstanding post, and in which said means for mounting said magazine for rotation on said frame includes a bore for receiving said upstanding post to permit said magazine to be removed from said instrument when desired.

11. The instrument in accordance with claim 7 in which said jaw actuating means includes:
a pair of actuating members pivotally mounted to said frame, each said actuating member having a forward distal end portion adapted to engage one of said jaws and having a rear portion extending rearwardly and outwardly away from said one jaw; and
first and second handles mounted to said frame for pivotal movement, each of said first and second handles including an engaging portion extending beyond its pivot axis and adapted to engage said rear portion of one of said actuating members whereby, when said first and second handles are moved toward each other, said engaging portions of each of said first and second handles moves outwardly to engage said rear portions of said actuating members to force said forward distal end portions of said actuating members against said first and second jaws to move said jaws toward each other from said open position into said closed position.

12. The instrument in accordance with claim 7 in which said means for releasably retaining said magazine against inadvertent rotation includes spring means carried on said frame for engaging one of said ratchet teeth when said magazine is rotated to align any one of said magazine clip storage regions with said first and second jaws.

13. The instrument in accordance with claim 11 in which said clip pushing means includes:
a wheel mounted for rotation to said frame;
a flexible pusher member secured to and partially wound around said wheel, said flexible pusher member having at least a forward end adapted to enter into one of said magazine clip storage regions in registration with said jaws and to move said clip out of said clip storage region into said jaws;
a circular gear connected with said wheel for rotation therewith; and
a gear segment mounted on one of said first and second handles and engaged with said circular gear for (1) rotating said wheel in a first direction when said handles are moved together to withdraw said flexible pusher member from said jaws and behind said inner access opening of one of said clip storage regions in registration with said jaws and (2) rotating said wheel in a second, opposite direction when said handles are moved apart whereby said flexible pusher member is advanced through one of said clip storage regions in registration with said jaws and between said jaws to push one of said clips into position at said jaws.

14. The instrument in accordance with claim 13 in which said frame includes a guide channel rearwardly of said magazine for guiding said flexible pusher member.

15. The instrument in accordance with claim 13 in which said frame includes a cover plate releasably disposed over said magazine and in which said cover plate includes a downwardly projecting guide member defining a guide channel for guiding said flexible pusher member adjacent the inner radius of said circular array of clip storage regions in registration with said jaws.

16. A medical instrument for applying a plurality of ligating clips seriatim about tissue wherein each said clip is initially provided in an open state, each said open clip comprising first and second legs joined at their proximal ends by a resilient hinge and being spaced apart at their distal ends with said legs having latch means at said distal ends for holding said clip closed in clamping engagement about said tissue when said legs are squeezed together, said instrument comprising:
a frame;
first and second jaws mounted to said frame in confronting relationship for movement away from each other into an open position to receive one of said clips and toward each other into a closed position for closing and latching said one clip;
jaw biasing means for biasing said jaws outwardly away from each other from said closed position and into said open position;
jaw actuating means for being operated to permit the movement of said jaws away from each other into said open position under the influence of said jaw biasing means and for being operated through a lost motion phase to effect movement of said jaws toward each other from said open position into said closed position following the termination of said lost motion phase;
a magazine and means for mounting said magazine on said frame for rotation relative to said frame, said magazine defining a plurality of clip storage regions arranged in a generally circular array, each said clip storage region defining an inner access opening at an inner radius of said circular array and an outer access opening at an outer radius of said array, each said clip storage region being adapted to hold one of said clips with said clip hinge adjacent said inner access opening and with said clip leg distal ends adjacent said outer access opening;

means carried on said frame for releasably retaining said magazine against inadvertent rotational movement after said magazine has been rotated to align any one of said magazine clip storage regions with said first and second jaws;

magazine rotating means responsive to the operation of the said jaw actuating means to close said jaws for incrementally rotating said magazine to move one of said clip storage regions out of registration with said jaws and to move the next adjacent clip storage region into registration with said jaws; and clip pushing means responsive to said jaw actuating means for (1) advancing into one of said magazine clip storage regions in registration with said jaws and moving said clip out of said clip storage region and into position between said jaws when said jaw actuating means is operated to permit the opening of said jaws, and (2) withdrawing from said jaws and behind said inner access opening of one of said clip storage regions in registration with said jaws as said jaw actuating means is operated through said lost motion phase prior to the closure of said jaws.

17. The instrument in accordance with claim 16 in which said magazine rotating means includes a circular array of ratchet teeth on said magazine, a pawl carried on said jaw actuating means for engaging said ratchet teeth when said jaw actuating means is operated to close said jaws; and biasing means associated with said pawl and with said jaw actuating means for biasing said pawl into engagement with said ratchet teeth.

18. A medical instrument for applying a plurality of ligating clips seriatim about tissue wherein each said clip is initially provided in an open state, each said open clip comprising first and second legs joined at a leg connection end of the clip and being spaced apart at their distal ends, said instrument comprising:

a frame;

first and second jaws mounted to said frame in confronting relationship for movement away from each other into an open position to receive one of said clips and toward each other into a closed position for closing said one clip;

jaw biasing means for biasing said jaws outwardly away from each other from said closed position and into said open position;

jaw actuating means for being operated to permit the movement of said jaws away from each other into said open position under the influence of said jaw biasing means and for being operated through a lost motion phase to effect movement of said jaws toward each other from said open position into said closed position following the termination of said lost motion phase;

a magazine and means for mounting said magazine on said frame for rotation relative to said frame, said magazine defining a plurality of clip storage regions arranged in a generally circular array, each said clip storage region defining an inner access opening at an inner radius of said circular array and an outer access opening at an outer radius of said array, each said clip storage region being adapted to hold one of said clips with the leg connection end of said clip adjacent said inner access opening and with said clip leg distal ends adjacent said outer access opening;

means carried on said frame for releasably retaining said magazine against inadvertent rotational movement after said magazine has been rotated to align any one of said magazine clip storage regions with said first and second jaws;

magazine rotating means responsive to the operation of the said jaw actuating means to close said jaws for incrementally rotating said magazine to move one of said clip storage regions out of registration with said jaws and to move the next adjacent clip storage region into registration with said jaws; and clip pushing means responsive to said jaw actuating means for (1) advancing into one of said magazine clip storage regions in registration with said jaws and moving said clip out of said clip storage region and into position between said jaws when said jaw actuating means is operated to permit the opening of said jaws, and (2) withdrawing from said jaws and behind said inner access opening of one of said clip storage regions in registration with said jaws as said jaw actuating means is operated through said lost motion phase prior to the closure of said jaws.

* * * * *